(12) United States Patent
Lemaire (10) Patent No.: US 7,537,615 B2
(45) Date of Patent: May 26, 2009

(54) INTERVERTEBRAL DISK PROSTHESIS

(75) Inventor: Jean-Philippe Lemaire, Saulon la Chapelle (FR)

(73) Assignee: Eden Spine Europe SA, Geneva (CH)

( * ) Notice: Subject to any disclaimer, the term of this patent is extended or adjusted under 35 U.S.C. 154(b) by 154 days.

(21) Appl. No.: 11/183,827

(22) Filed: Jul. 19, 2005

(65) Prior Publication Data

US 2006/0235526 A1 Oct. 19, 2006

(30) Foreign Application Priority Data

Apr. 15, 2005 (EP) .................................. 05008271

(51) Int. Cl.
*A61F 2/44* (2006.01)
(52) U.S. Cl. ................. 623/17.15; 623/17.14
(58) Field of Classification Search .... 623/17.11–17.16
See application file for complete search history.

(56) References Cited

U.S. PATENT DOCUMENTS

| | | | |
|---|---|---|---|
| 5,401,269 A * | 3/1995 | Buttner-Janz et al. .... | 623/17.15 |
| 2004/0002761 A1 | 1/2004 | Rogers et al. | |
| 2004/0243240 A1 * | 12/2004 | Beaurain et al. ......... | 623/17.14 |
| 2005/0251262 A1 * | 11/2005 | De Villiers et al. ....... | 623/17.14 |
| 2006/0069437 A1 * | 3/2006 | Weber ..................... | 623/17.14 |
| 2006/0095132 A1 * | 5/2006 | Kirschman ............... | 623/17.14 |

FOREIGN PATENT DOCUMENTS

| | | |
|---|---|---|
| FR | 2 659 226 | 9/1991 |
| FR | 2 846 550 | 5/2004 |
| WO | WO 02/089701 | 11/2002 |

* cited by examiner

*Primary Examiner*—Eduardo C Robert
*Assistant Examiner*—Jerry Cumberledge
(74) *Attorney, Agent, or Firm*—Young & Thompson (57) ABSTRACT

The intervertebral disk prosthesis comprises first and second parts (2, 3) intended to be attached respectively to two adjacent vertebrae, an intermediate part (4) inserted between the first and second parts (2, 3) and comprising articular surfaces (9, 10) that cooperate with respective articular surfaces (6, 8) of the first and second parts (2, 3), and means (11, 12) for coupling the first part (2) and the intermediate part (4). The coupling means (11, 12) are arranged to leave the intermediate part (4) free relative to the first part (2) during a first phase of a tilting movement of the first part (2) relative to the second part (3), but to displace the intermediate part (4) toward an end (E2) of the prosthesis that is opposite to an end (E1) toward which the first part (2) is displaced by tilting relative to the second part (3), during a second phase of the tilting movement of the first part (2).

18 Claims, 13 Drawing Sheets

INTERVERTEBRAL DISK PROSTHESIS

FIELD OF THE INVENTION

This invention relates to a prosthesis that is intended to replace the intervertebral disk.

BACK GROUND OF THE INVENTION

The intervertebral disk is a fibrocartilaginous disk that ensures the connection between two adjacent vertebrae of the vertebral column. The unit that is formed by the intervertebral disk and the two corresponding adjacent vertebrae is called "vertebral segment".

The intervertebral disk prostheses generally consist of two plates, referred to as upper and lower plates, that are opposite one another and intended to be attached to two respective adjacent vertebrae, referred to as upper and lower vertebrae, and a core that is inserted between the two plates. The plates are generally metal, and the core is made of metal or a polymer, such as high-density polyethylene. Two main types of such prostheses exist to date:

the so-called non-constraint prostheses, in which the core is free relative to the two plates and comprises generally convex articular surfaces cooperating with generally concave articular surfaces of the plates;

the so-called constraint prostheses, in which the core is solid with one of the two plates and comprises a generally convex articular surface cooperating like a ball joint with a generally concave articular surface of the other plate.

In the first type of prosthesis, the core has five degrees of freedom, three in rotation and two in translation, relative to a stationary reference. During a flexion/extension movement (patient leaning forward/backward respectively) or a lateral tilting movement (patient leaning to the side), the upper plate is tilted relative to the lower plate by sliding on the core toward one end of the prosthesis. This tilting movement of the upper plate, which can be seen as a combination of a rotation around a horizontal axis that passes through the center of gravity of the unit formed by the upper plate and the upper vertebra and of a translation toward the above-mentioned end of the prosthesis, entails a translation of the core toward the opposite end of the prosthesis, which translation thus compensates for the translation of the upper plate to the first end. During a twisting movement of the patient, the upper plate pivots relative to the lower plate in the horizontal plane by articulating with the core. Coupling means between the plates and the core, such as central pins that project on the core or the plates and cooperate with corresponding cavities that are formed in the plates or the core respectively, are in some cases provided for limiting the amplitude of the movements of the prosthesis or simply for avoiding the ejection of the core. Examples of such non-constraint prostheses are described in U.S. Pat. No. 5,401,269.

In the second type of prosthesis, the core has three degrees of freedom in rotation and no degree of freedom in translation. An example of such constraint prostheses is described in Patent Application FR 2 659 226.

Neither of these two types of prostheses faithfully reproduces the natural biomechanics of the vertebral segment. These prostheses are actually based on a linear conception of the biomechanics whereas the natural biomechanics of the vertebral segment, more specifically the function that connects the displacement of the vertebral segment to the applied force, is non-linear.

OBJECT OF THE INVENTION

A purpose of this invention is to provide an intervertebral disk prosthesis that makes it possible to reproduce more faithfully the natural biomechanics of the vertebral segment. For this purpose, an intervertebral disk prosthesis as defined in attached claim 1 is proposed, whereby special embodiments are defined in the dependent claims.

BRIEF DESCRIPTION OF THE DRAWINGS

Other characteristics and advantages of this invention will emerge from reading the following detailed description given in reference to the attached drawings in which.

DETAILED DESCRIPTION OF THE INVENTION

In reference to FIGS. 1 to 4, an intervertebral disk prosthesis 1 according to a first embodiment of the invention comprises an upper plate 2, a lower plate 3, and a core 4. Upper plate 2 comprises, on its upper face, anchoring points 5 for its attachment to a so-called upper vertebra, and on its lower face, a concave articular surface 6, typically in the form of a spherical portion. Lower plate 3 comprises, on its lower face, anchoring points 7 for its attachment to a so-called lower vertebra, adjacent to the upper vertebra, and on its upper face, a concave articular surface 8, typically in the form of a spherical portion. Core 4 is inserted between plates 2, 3 and comprises, respectively on its upper and lower faces, two opposite convex articular surfaces 9, 10 that cooperate with concave articular surfaces 6, 8 of plates 2, 3. Each of the two articular surfaces 9, 10 of core 4 is congruent with corresponding articular surface 6, 8 of plate 2, 3. Preferably, for a reason that will be indicated below, the radius of curvature R1 of articular surfaces 6, 9 is less than the radius of curvature R2 of articular surfaces 8, 10. Plates 2, 3 are made of, for example, a metal of Co—Cr-Mb alloy or titanium type, and core 4 is made of metal or a polymer of the high-density polyethylene type.

Core 4 is coupled to plates 2, 3 respectively by first and second coupling means. The first coupling means comprise a pin 11 that projects on a front peripheral portion of the lower face of upper plate 2 and a cavity 12 that is formed in core 4 and that opens onto articular surface 9 of the latter, whereby cavity 12 receives pin 11. By "peripheral portion" is meant a portion that is not traversed by the axis A of the prosthesis. Pin 11 is furthermore located in the sagittal plane passing through axis A and is tilted relative to upper plate 2 and directed toward said axis A. Pin 11 can be formed integral with upper plate 2 or attached to the latter by, for example, welding. Cavity 12 has approximately the same shape, for example tapered, as pin 11, but its section is larger than that of pin 11 so as to allow travel of pin 11 and therefore of upper plate 2 relative to core 4 in the sagittal, frontal and coronal planes. The second coupling means comprise a rail 13 that is formed integral with lower plate 3 or attached to the latter by, for example, welding and that extends in a sagittal direction on articular surface 8 of said lower plate 3. This rail 13, located in the rear portion of the prosthesis, defines an inclined support surface 14 that connects the tip of rail 13, at the rear edge of lower plate 3, to the central portion of articular surface 8 of plate 3. This rail 13 cooperates with a groove 15 of corresponding shape, itself also comprising an inclined support surface 16, formed in lower articular surface 10 of core 4. Groove 15 has a wider section than that of rail 13 so as to allow axial-rotation travel, i.e., rotation travel around axis A, of core 4 relative to lower plate 3 (twisting) as well as lateral-tilting travel.

Figure 1:
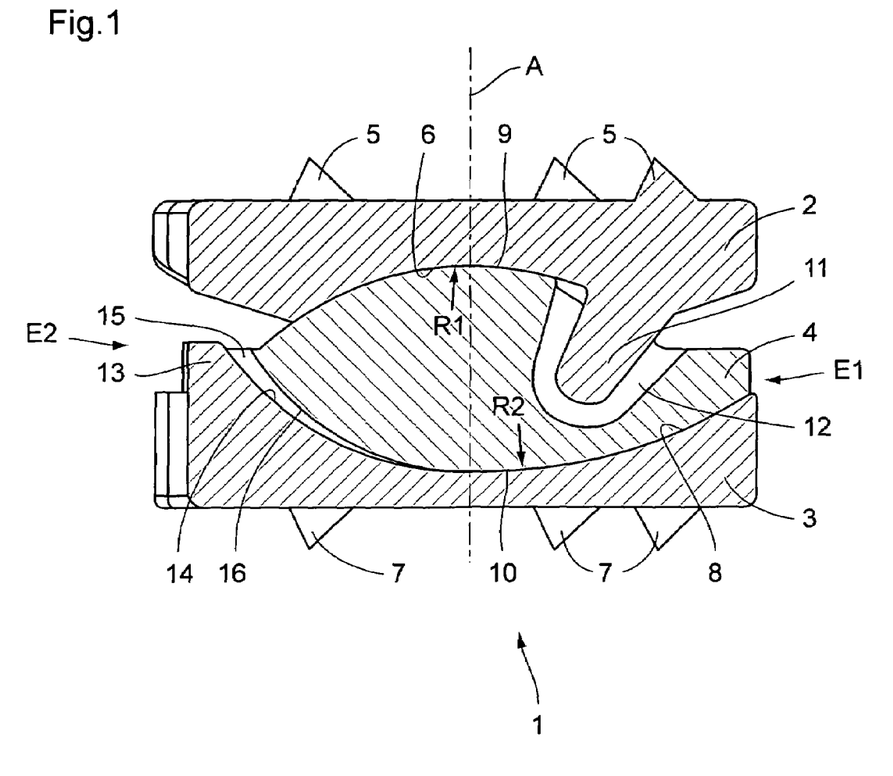
FIG. 1 is a sagittal cutaway view of an intervertebral disk prosthesis according to a first embodiment of the invention, in neutral position.
Figure 2:
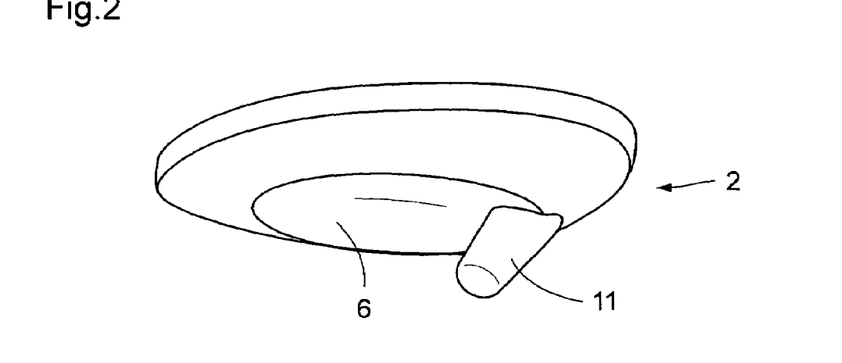
FIGS. 2 and 3 are perspective views that respectively show an upper plate and a lower plate of the prosthesis according to the first embodiment.
Figure 3:
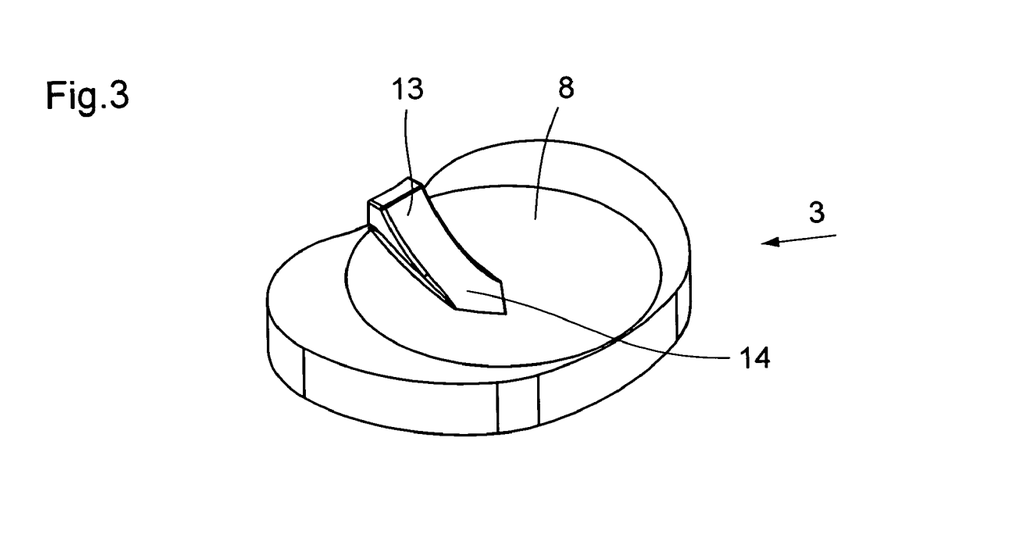
Figure 4A:
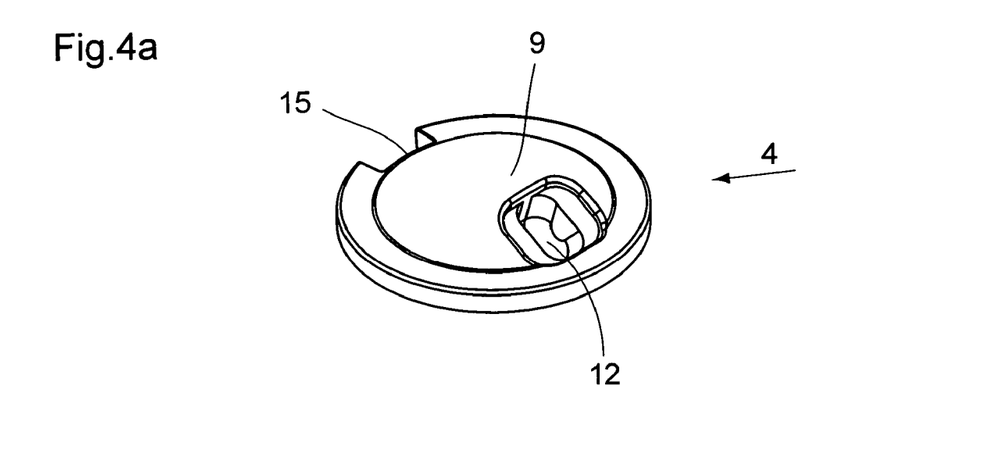
FIGS. 4a and 4b are respectively a top perspective view and a rear view of a core of the prosthesis according to the first embodiment.
Figure 4B:
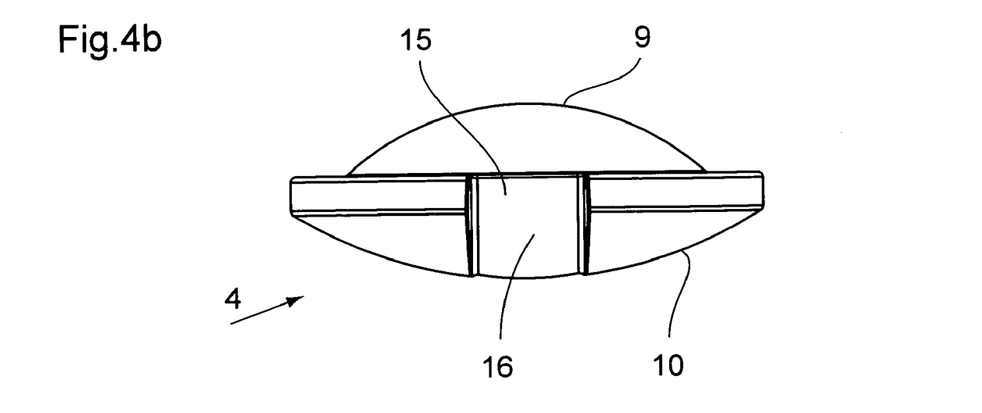
Figure 5A:
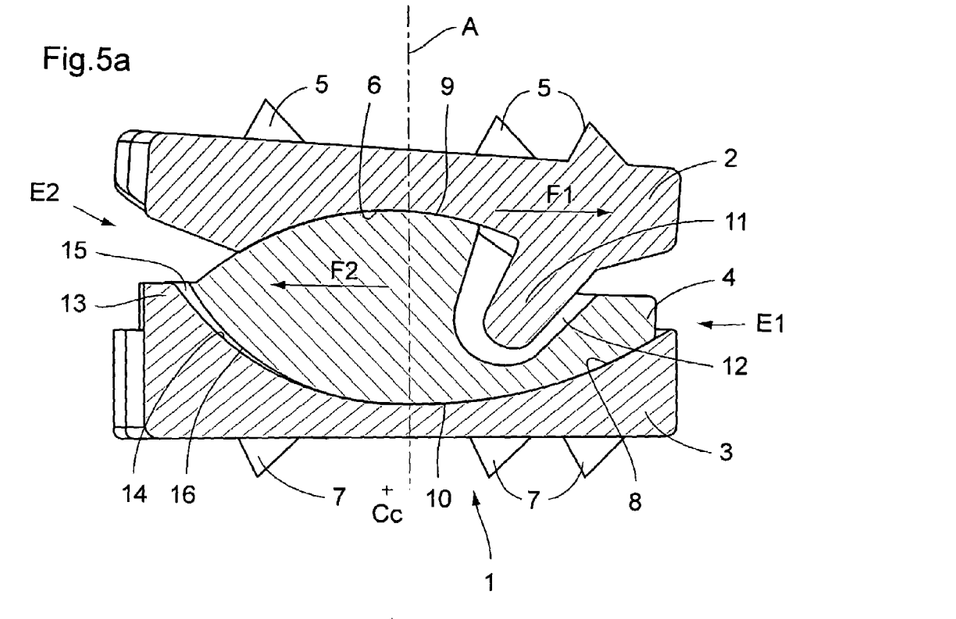
FIG. 5a is a diagrammatic sagittal cutaway view of the prosthesis according to the first embodiment in the process of carrying out a first phase of a flexion movement.
Figure 5B:
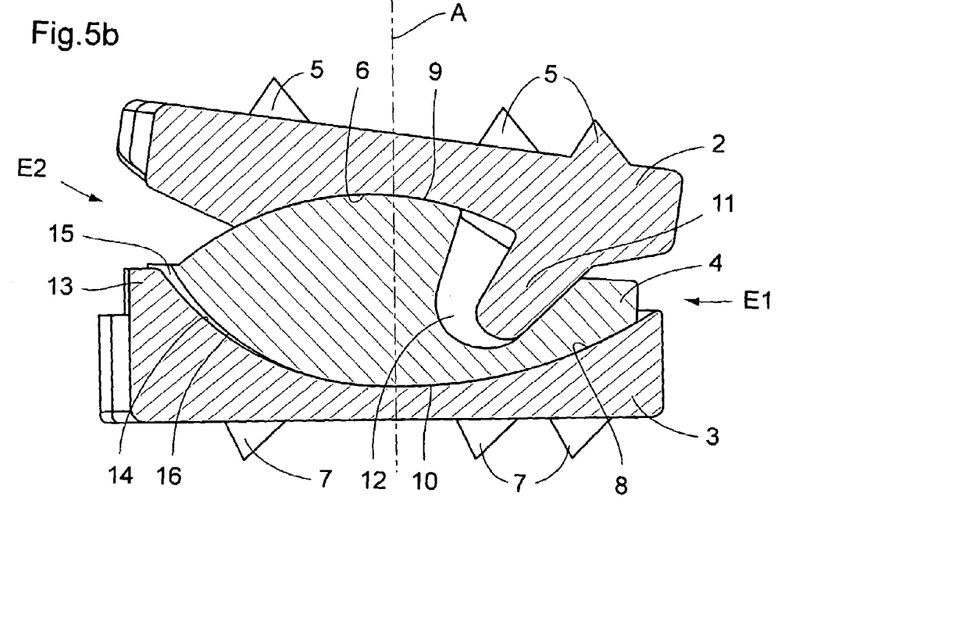
FIG. 5b is a diagrammatic sagittal cutaway view of the prosthesis according to the first embodiment in a position that corresponds to the end of the first phase of the flexion movement.
Figure 6:
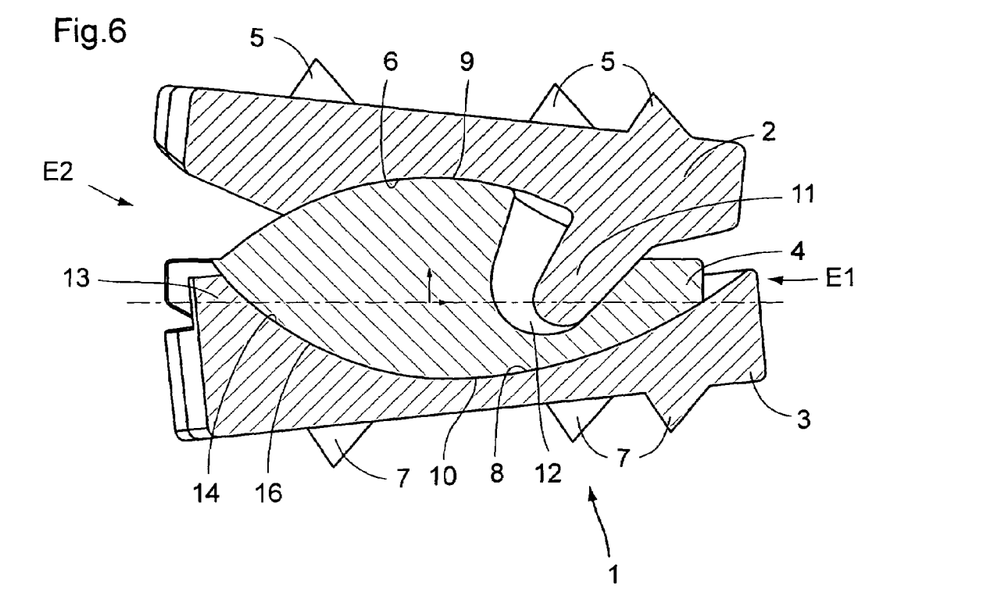
FIGS. 6 and 7 are diagrammatic sagittal cutaway views that show the prosthesis according to the first embodiment in the process of carrying out a second phase of a flexion movement, respectively of an extension movement.
Figure 7:
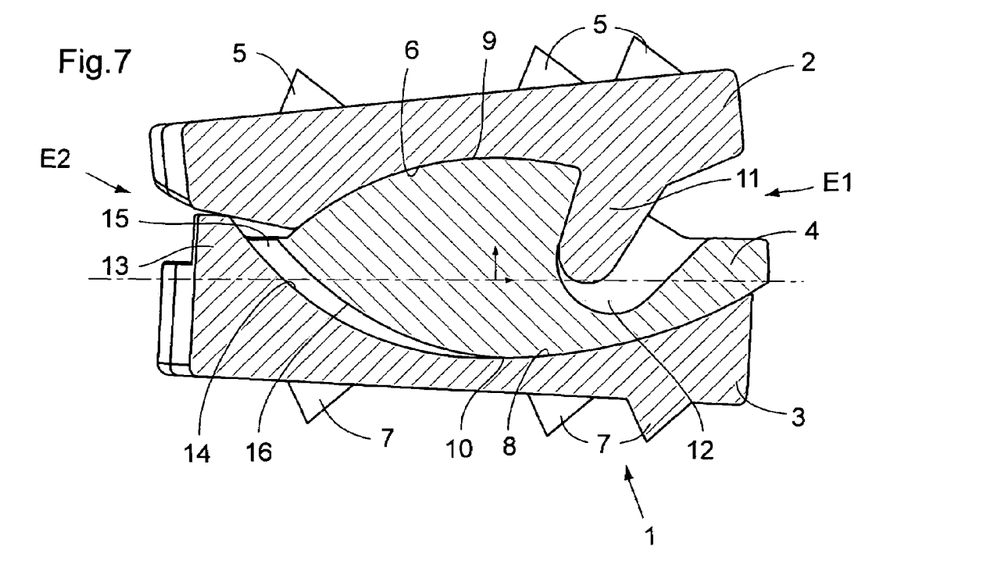

According to the invention, the tilting movements of upper plate 2 of the prosthesis relative to lower plate 3 in the sagittal plane (flexion/extension) and/or in the frontal plane (lateral tilting) break down into two phases:

a first phase during which upper plate 2 slides on core 4, pin 11 moving freely in cavity 12; and a second phase, which begins just after pin 11 has entered into contact with the inside wall of cavity 12 (cf. FIG. 5b), during which upper plate 2 drives with it core 4 via pin 11 (cf. FIG. 6: prosthesis in flexion; FIG. 7: prosthesis in extension).

During the first phase, upper plate 2, with the so-called upper vertebra to which it is attached, carries out a movement of rotation around the center of curvature Cc of articular surfaces 6, 9. This movement of rotation tends to displace upper plate 2 toward an end E1 of the prosthesis, as shown by arrow F1 in FIG. 5a. However, as core 4 is free relative to plates 2, 3, upper plate 2, by sliding on core 4 toward end E1, drives core 4 toward the opposite end E2 of the prosthesis, as shown by arrow F2, which displaces center of rotation Cc of upper plate 2 toward end E2 and compensates for the above-mentioned displacement of upper plate 2 toward end E1. This movement of the prosthesis during this first phase is identical to that of a non-constraint prosthesis. It can be viewed as a combination of a rotation of the upper plate 2—upper vertebra unit around a horizontal axis that passes through its center of gravity and of a translation of this unit, whereby this combination of movements imitates the natural rotation-translation combined movement of the upper vertebra. During the second phase, upper plate 2 and core 4 form a solid unit that articulates in the manner of a ball joint with lower plate 3, i.e., rotates around the center of curvature of articular surfaces 8, 10 (FIGS. 6, 7).

Figure 21:
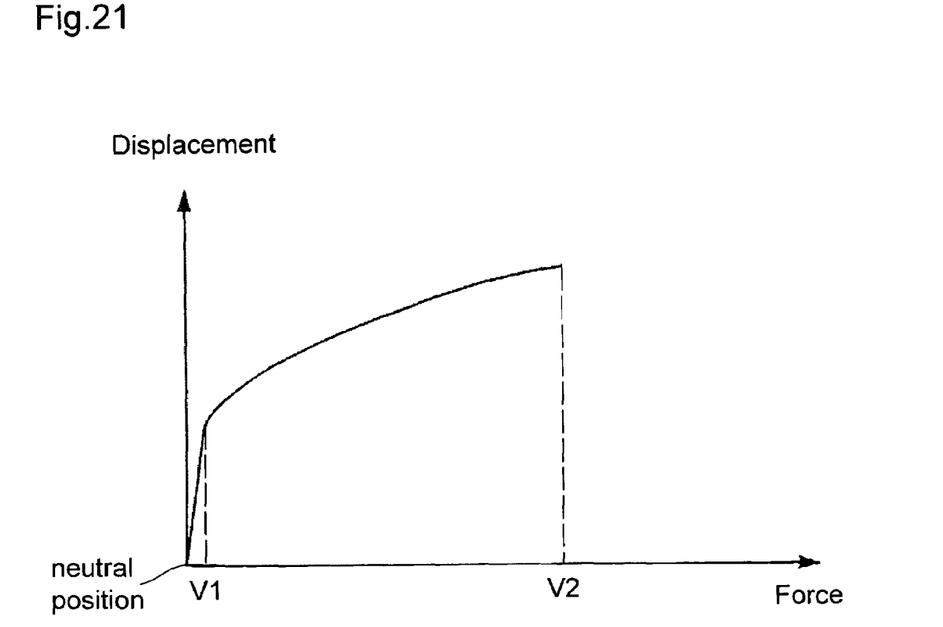
FIG. 21 shows the curve of the natural displacement of a vertebra versus the force that is applied to the latter.

During the first phase, a weak force applied to the upper plate 2—upper vertebra unit is sufficient to cause a significant tilting displacement of this unit. In the second phase, much greater additional force has to be applied to obtain the same displacement amplitude as in the first phase, because upper plate 2 drives core 4 and therefore has to exert greater stress. This is in accordance with the natural biomechanics of the vertebral segment. Indeed, as shown in FIG. 21, the curve of the physiological tilting displacement of a vertebra versus the force that is applied to the latter has a first linear portion corresponding to forces ranging from 0 to a value V1 and exhibiting a high slope, and a second non-linear portion corresponding to forces ranging from the value V1 to the maximum physiological force V2 and whose slope is much less than that of the linear portion and decreasing. In the present invention, the first phase of the tilting movement of upper plate 2 relative to lower plate 3 corresponds approximately to the linear portion of the above-mentioned curve while the second phase of this movement corresponds approximately to the non-linear portion of this curve. Values V1 and V2 vary depending on the patient. The respective angular ranges of the first and second phases of movement of the prosthesis should therefore be adapted to the patient by manipulating the respective sections of pin 11 and cavity 12. In typical but non-limiting embodiments of the present invention, the first phase corresponds to an angular tilting range of upper plate 2 relative to lower plate 3, from its neutral position shown in FIG. 1, of about 4 to 8°, and preferably of about 5 to 7°, and the second phase to an angular tilting range of upper plate 2 relative to lower plate 3 of about 3 to 7°, preferably of about 4 to 6°. The first phase typically can correspond to about 40 to 60% of the maximum tilting angle of upper plate 2 relative to lower plate 3, and the second phase to the remaining 60 to 40%.

Another advantage of this movement in two phases of upper plate 2 relative to lower plate 3 is that it makes it possible to control the displacement of core 4 and thus to limit the constraints, in particular the surface or pinpoint hyper-pressures and the hypopressures, that can be exerted on the rear articular system, because this core 4 is made solid with upper plate 2 during the second phase.

In addition, it will be noted that coupling means 11, 12, 13, 15 of the prosthesis according to the invention allow twisting movements (axial rotation of upper plate 2 relative to lower plate 3) only within determined limits. This also contributes to protecting the rear articular system.

In addition to their function of limiting the axial rotation of core 4 relative to lower plate 3, rail 13 and corresponding groove 15 cooperate together during flexion movements to slightly raise the center of gravity of core 4, in line with the physiological movement, by the inclined support surface 16 of groove 15 sliding on inclined support surface 14 of rail 13 (cf. FIG. 6).

Furthermore, because congruent articular surfaces 6, 9 have a radius of curvature R1 that is less than radius of curvature R2 of congruent articular surfaces 8, 10, the rotation component of the tilting movements of upper plate 2 is favored relative to the translation component.

The prosthesis according to the present invention also offers the advantage of limiting the risks of core 4 being ejected, thanks in particular to the cooperation between pin 11 and cavity 12.

Figure 8:
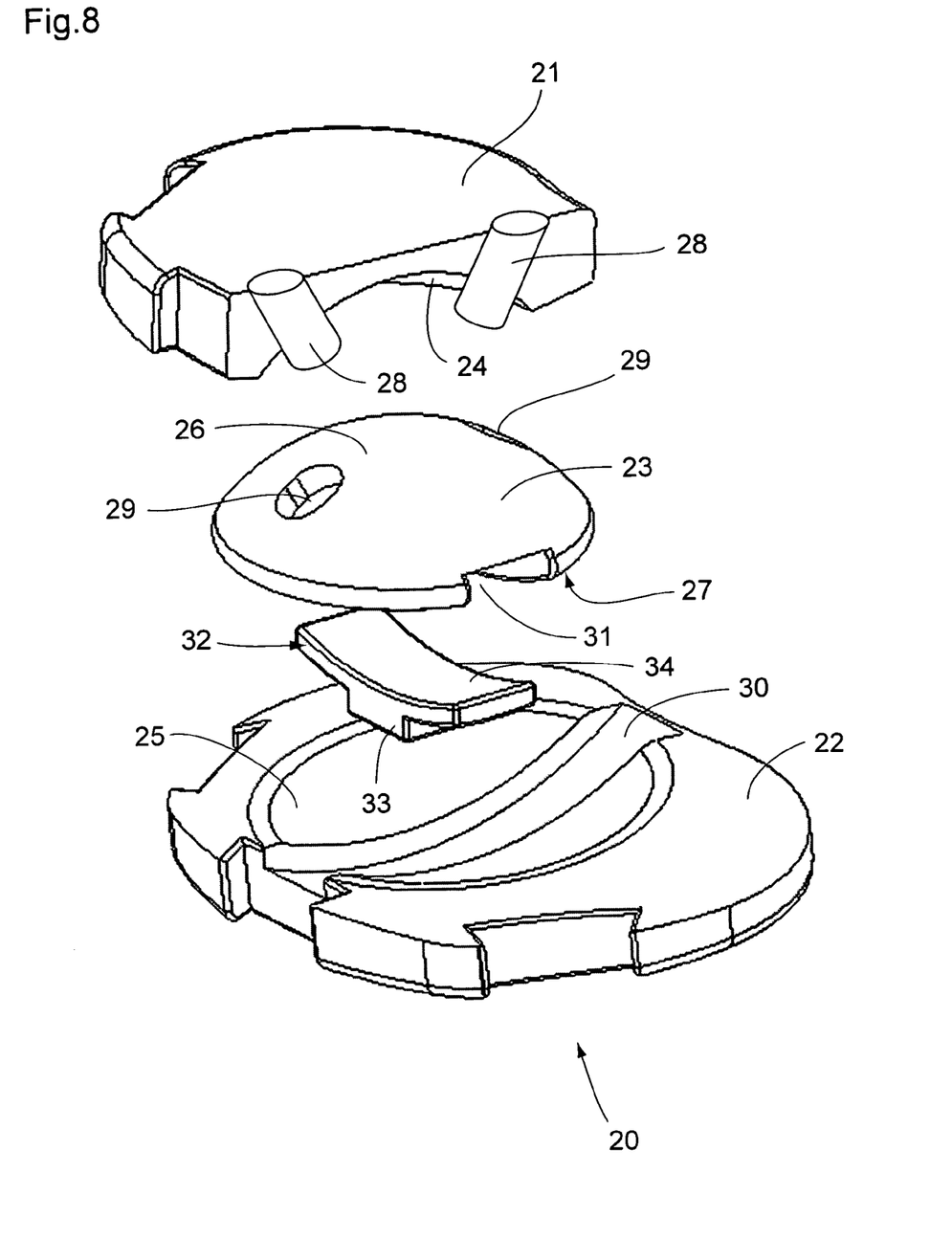
FIG. 8 is an exploded perspective view, in partial cutaway, of an intervertebral disk prosthesis according to a second embodiment of the invention.
Figure 9:
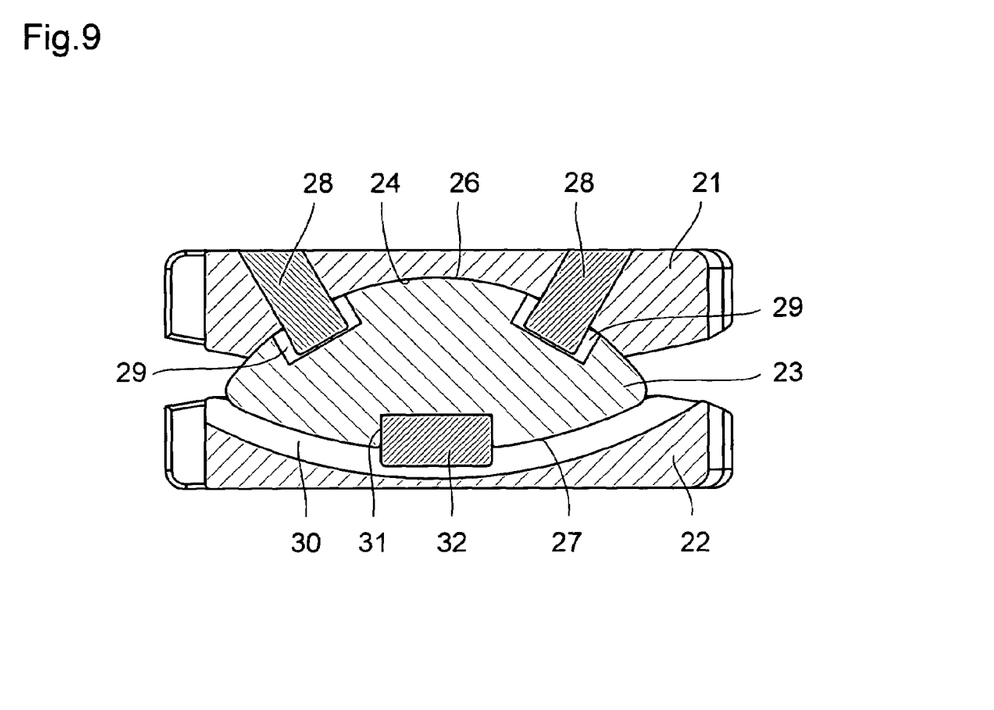
FIGS. 9 and 10 are sagittal and frontal cutaway views, respectively, showing the prosthesis according to the second embodiment in neutral position.
Figure 10:
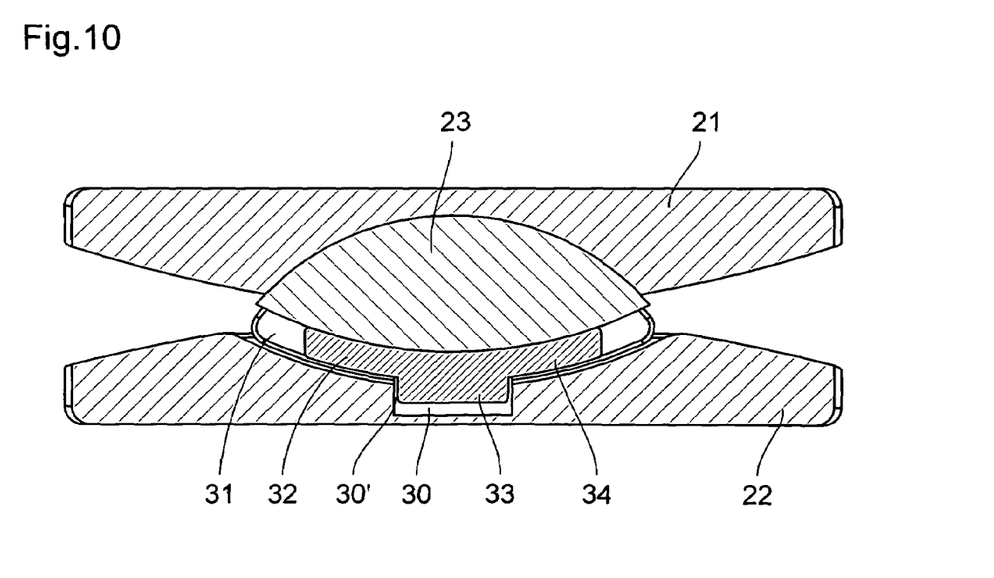

In reference to FIGS. 8 to 10, an intervertebral disk prosthesis 20 according to a second embodiment of the invention comprises upper and lower plates 21, 22 that are intended to be attached to two adjacent vertebrae, and a core 23 that is inserted between plates 21, 22. As in the first embodiment, upper and lower plates 21, 22 each comprise a concave articular surface 24, 25 that cooperates with a corresponding convex articular surface 26, 27 of core 23. Upper plate 21 and core 23 are coupled by first coupling means that comprise two tilted studs 28 that project on a peripheral portion of articular surface 24 of upper plate 21 and two tilted cavities 29 that are formed in articular surface 26 of core 23 and that receive studs 28. Studs 28 are located in the sagittal plane that passes through the axis of the prosthesis, directed toward said axis and placed on both sides of this axis symmetrically to one another. Studs 28 are attached in upper plate 21 by, for example, welding. Corresponding cavities 29 have a larger section that that of studs 28 so as to allow travel of upper plate 21 relative to core 23 in the sagittal, frontal and coronal planes.

Core 23 and lower plate 22 are coupled by second coupling means that comprise a first groove with a rectangular section 30 formed in articular surface 25 of lower plate 22 and extending in a sagittal direction, a second groove with a rectangular section 31 formed in articular surface 27 of core 23 and extending in a frontal direction, and a mobile intermediate guide part 32, in the form of a T, cooperating with the two grooves 30, 31. More specifically, the vertical branch 33 of guide part 32, which is shorter than the horizontal branch 34, is guided in first groove 30 while horizontal branch 34 is guided in second groove 31. First groove 30 is wider than vertical branch 33 of guide part 32 so as to define a play 30' (visible only in FIG. 10) that allows axial-rotation travel between core 23 and lower plate 22 (twisting).

Figure 11:
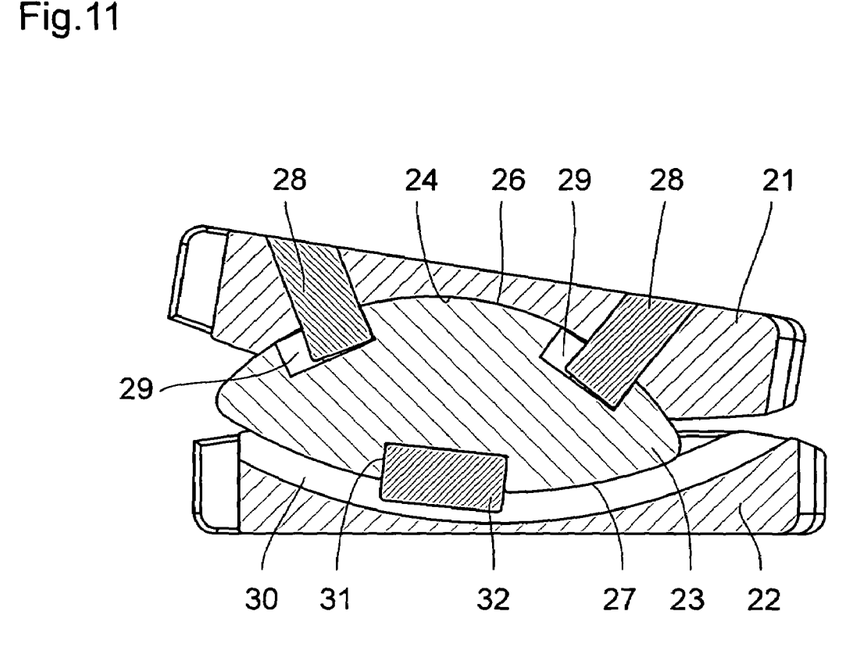
FIGS. 11 and 12 are diagrammatic sagittal cutaway views showing the prosthesis according to the second embodiment in the process of carrying out a second phase of a flexion movement, respectively of an extension movement.
Figure 12:
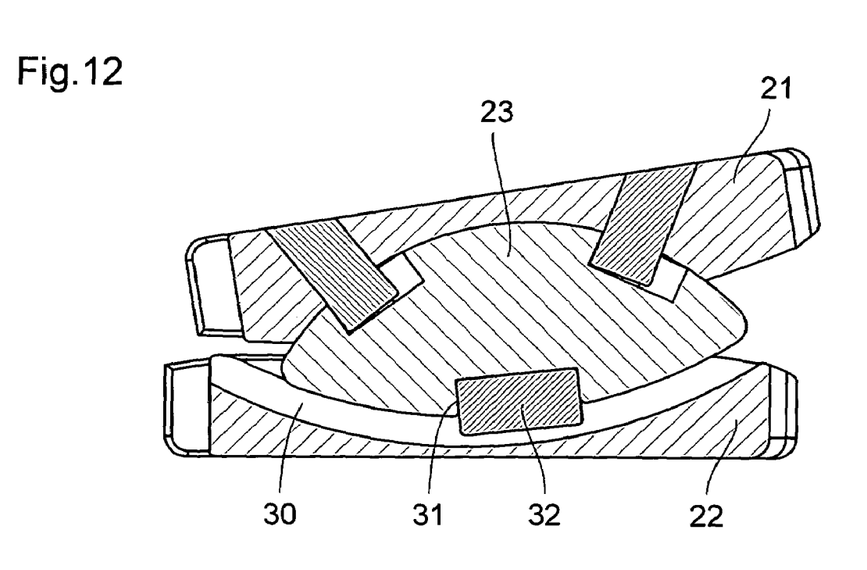
Figure 13:
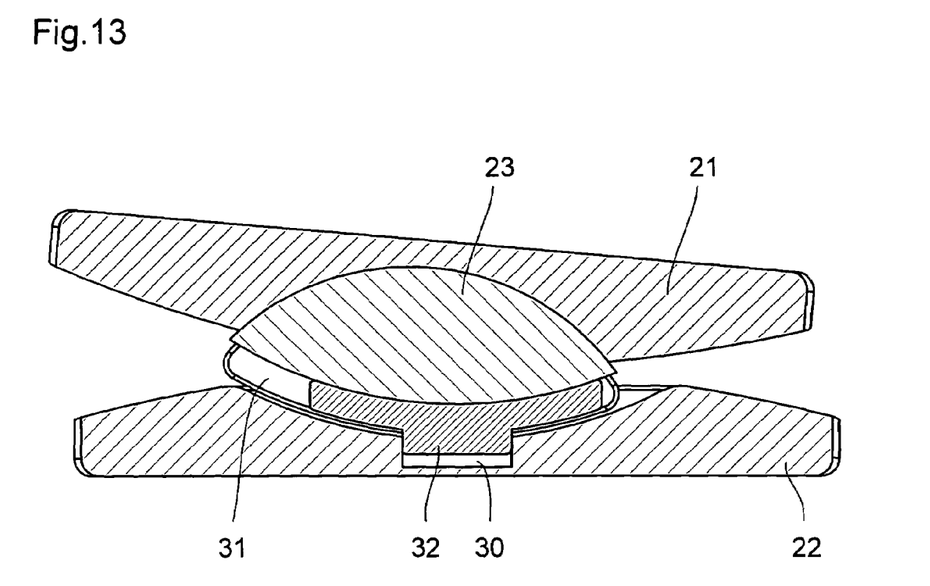
FIGS. 13 and 14 are diagrammatic frontal cutaway views that show the prosthesis according to the second embodiment in the process of carrying out a second phase of a lateral tilting movement toward the right, respectively toward the left.
Figure 14:
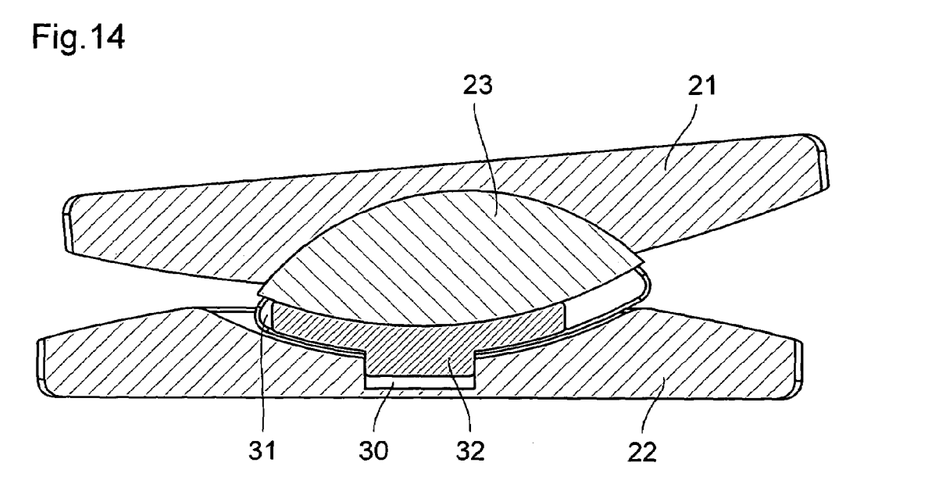

The movements of flexion, extension and lateral tilting of prosthesis 20 are similar to those of prosthesis 1, i.e., they are carried out in two phases, namely a first phase where the movement between upper plate 21 and core 23 is a non-constraint movement, whereby studs 28 are displaced freely in cavities 29, and a second phase where studs 28, abutting against the inside wall of their respective cavities 29, push core 23, thus making it solid with upper plate 21 (cf. FIG. 11: flexion; FIG. 12: extension; FIG. 13: lateral tilting to the right side; FIG. 14: lateral tilting to the left side). During the flexion/extension movements, guide part 32, guided by groove 30, is displaced with core 23 (FIGS. 11, 12). During lateral tilting movements, guide part 32 remains stationary relative to lower plate 22 and guides the displacement of core 23 by its cooperation with groove 31 (FIGS. 13, 14). The twisting movements of prosthesis 20 (axial rotation of upper plate 21 relative to lower plate 22) are limited by coupling means 28-32.

Prosthesis 20 according to this second embodiment offers the advantage, relative to prosthesis 1 according to the first embodiment, of better controlling the movements of the prosthesis and therefore of reducing the constraints exerted on the rear articular system, by limiting the coupled movements (combinations of movements of flexion/extension, lateral tilting and axial rotation), thanks to guide part 32 and to associated grooves 30, 31 that guide the movements of the prosthesis.

Figure 15:
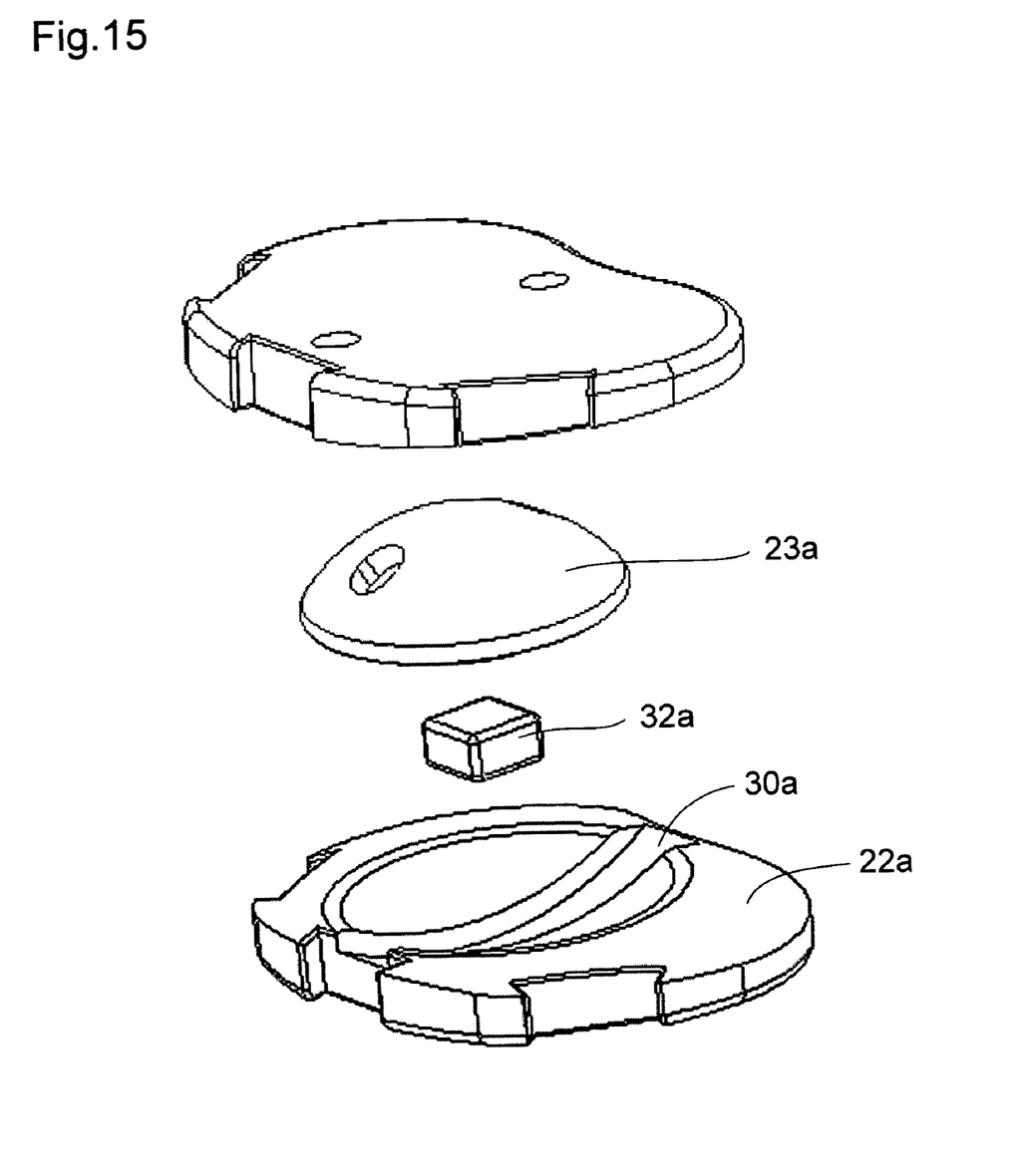
FIG. 15 is an exploded perspective view of a variant of the prosthesis according to the second embodiment.

In a variant of this second embodiment, shown in FIG. 15, guide part 32*a* is of rectangular parallelepipedic shape whose lower portion is received in a groove 30*a* of lower plate 22*a* that is oriented sagitally, and the upper portion is received in a groove (not visible) of core 23*a* that is oriented frontally.

Figure 16:
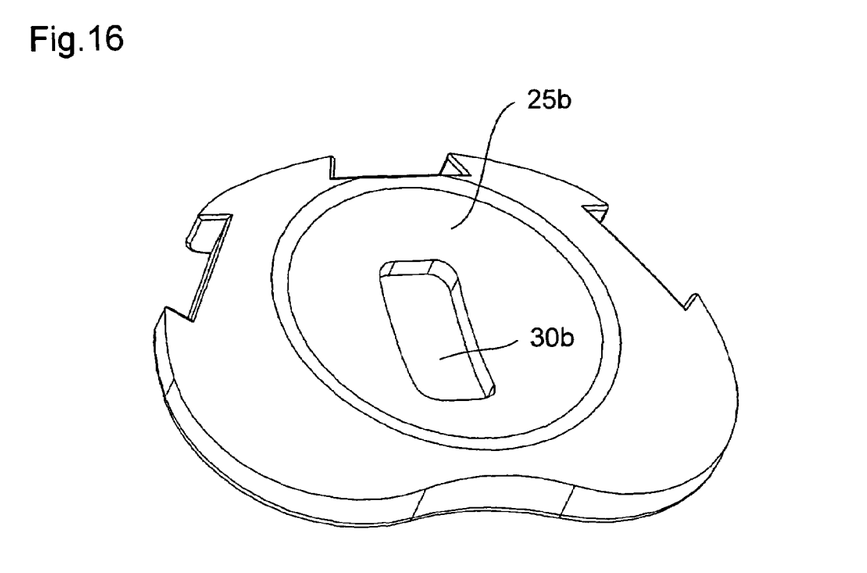
FIG. 16 is a top perspective view of a lower plate that is part of another variant of the prosthesis according to the second embodiment.

FIG. 16 shows a variant of lower plate 22 of the prosthesis according to the second embodiment, in which sagittal groove 30*b* is closed at its two ends and is completely inside the contour of articular surface 25*b* to limit the displacements of guide part 32 or 32*a* in the sagittal direction.

Figure 17:
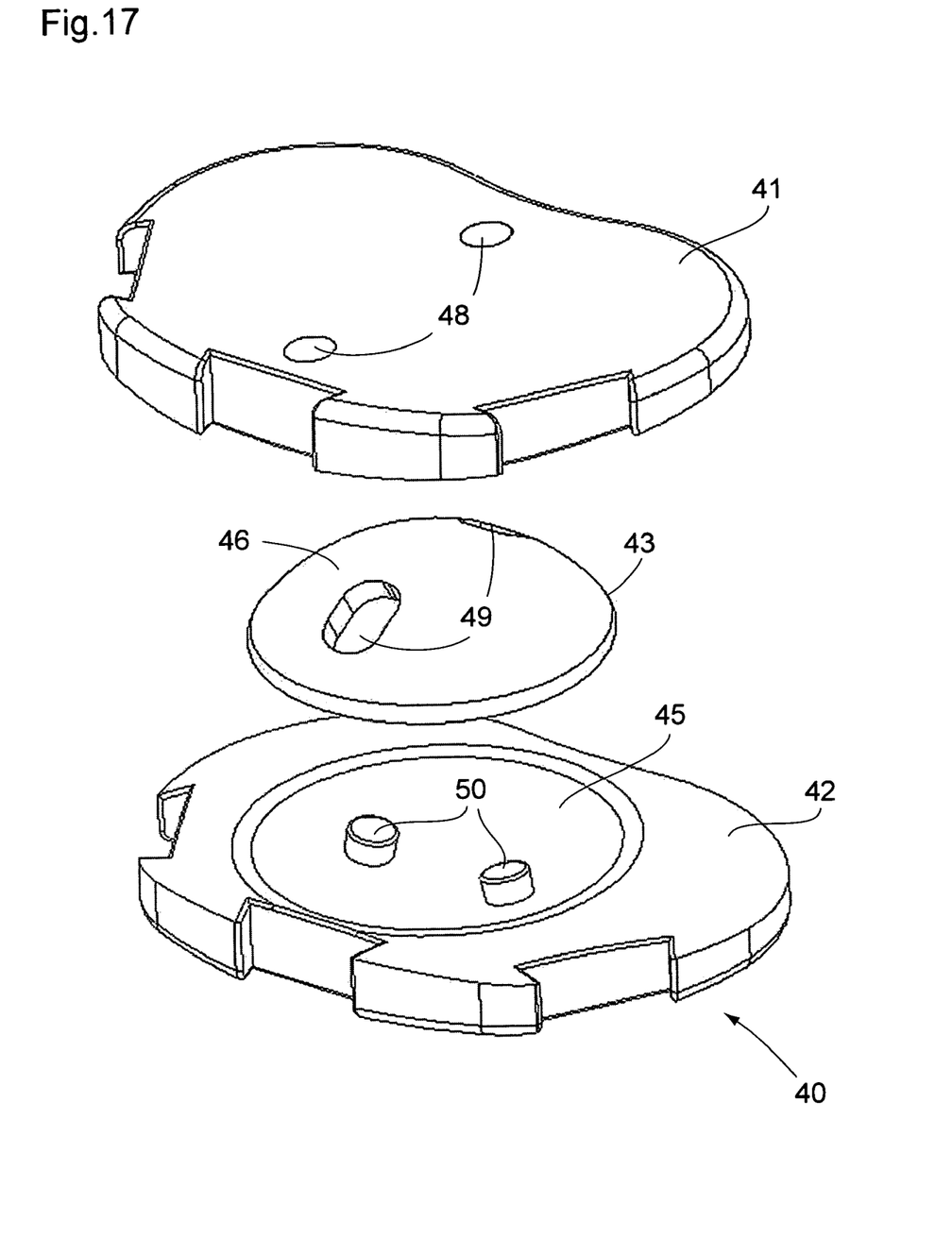
FIGS. 17 and 18 are top and bottom perspective views respectively, showing an intervertebral disk prosthesis according to a third embodiment of the invention.
Figure 18:
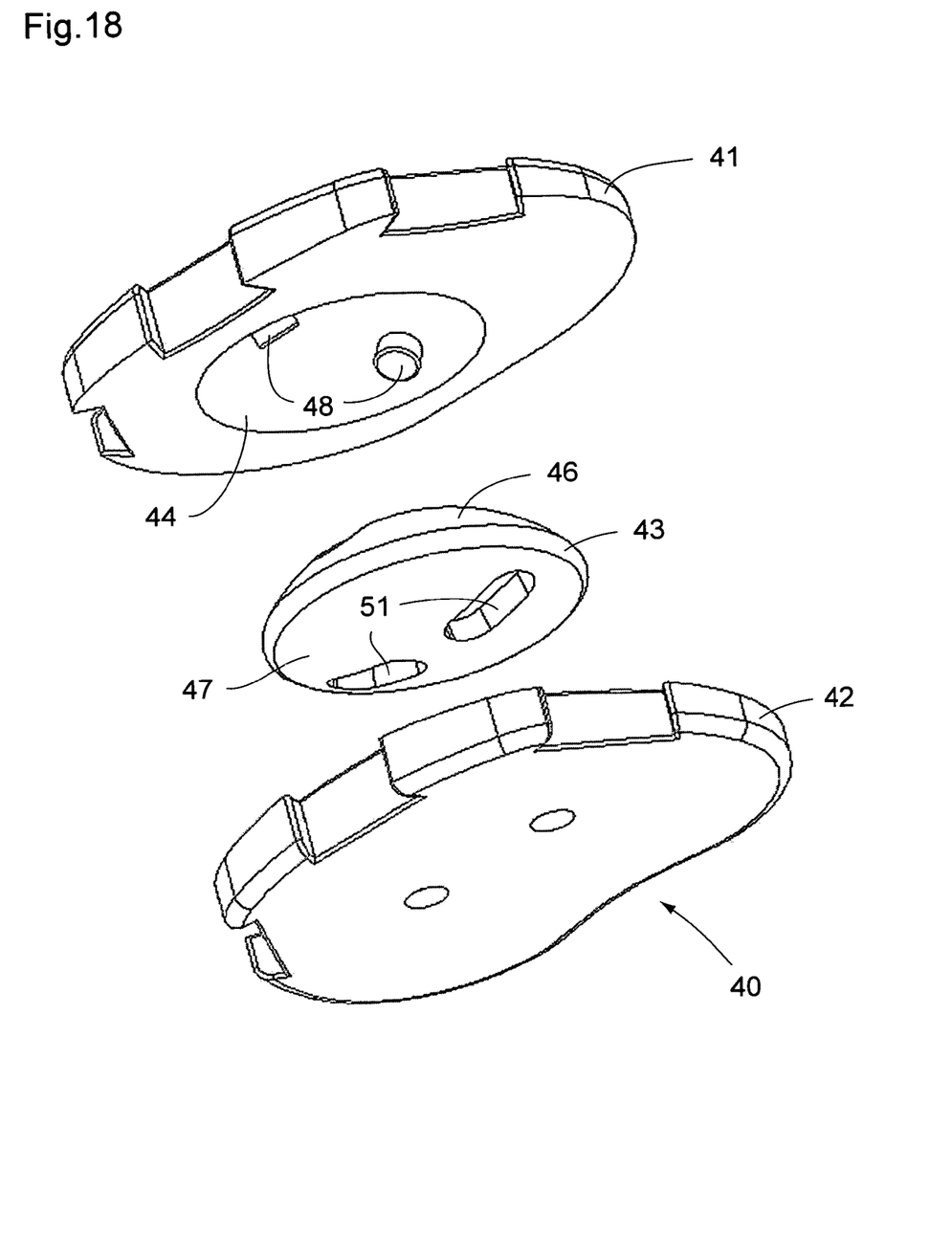

FIGS. 17 and 18 show an intervertebral disk prosthesis 40 according to a third embodiment of the present invention. Prosthesis 40 comprises an upper plate 41, a lower plate 42, and a core 43. Plates 41, 42 comprise respective concave articular surfaces 44, 45 that cooperate with respective convex articular surfaces 46, 47 of core 43. Upper plate 41 and core 43 are coupled by coupling means that comprise, as in the second embodiment, tilted studs 48 that project on a peripheral portion of articular surface 44 of upper plate 41 and corresponding tilted cavities 49 that are formed in articular surface 46 of core 43. Studs 48 are located in the sagittal plane that passes through the axis of the prosthesis, directed toward said axis and symmetrical to one another relative to said axis. Corresponding cavities 49 here have an oblong shape that is oriented in a sagittal direction.

Prosthesis 40 also comprises means for coupling core 43 and lower plate 42, constituted by tilted studs 50 that project on a peripheral portion of articular surface 45 of lower plate 42 and corresponding tilted cavities 51 that are formed in articular surface 47 of core 43. Studs 50 are located in the frontal plane that passes through the axis of the prosthesis, directed toward said axis and symmetrical to one another relative to said axis. Corresponding cavities 49 have an oblong shape that is oriented in a frontal direction.

The respective plays between studs 48 and cavities 49 and between studs 50 and cavities 51 are large enough to allow movements of flexion/extension and/or lateral tilting of upper plate 41 relative to lower plate 42 in two phases, namely a first phase during which studs 48 are displaced freely in cavities 49 and a second phase during which upper plate 41 drives core 43 via studs 48. During these tilting movements of upper plate 41, coupling means 50, 51 guide the movements of core 43. These coupling means 50, 51, with means 48, 49, also limit the axial rotation of upper plate 41 relative to lower plate 42.

Figure 19:
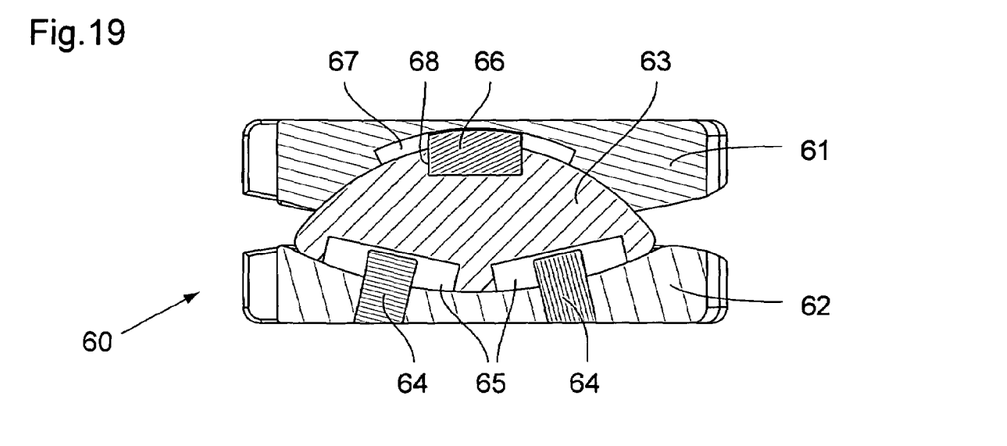
FIGS. 19 and 20 are a sagittal cutaway view and an exploded top perspective view, respectively, showing an intervertebral disk prosthesis according to a fourth embodiment of the invention.
Figure 20:
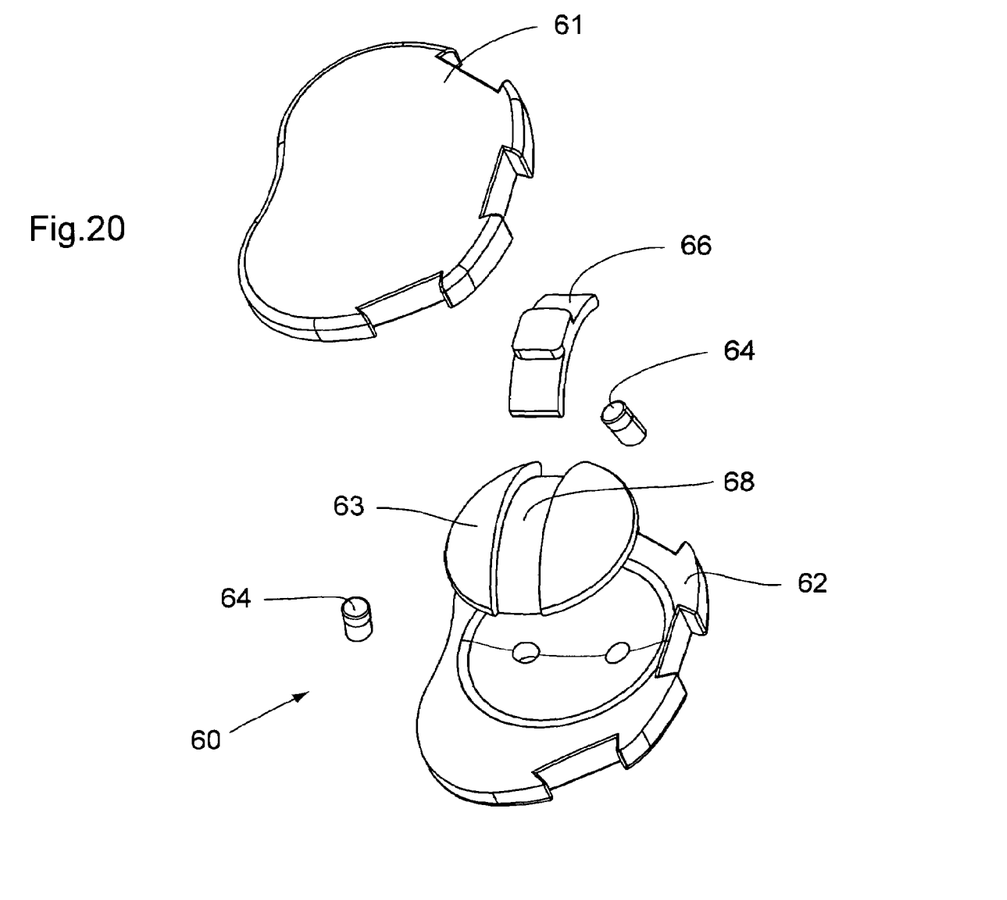

FIGS. 19 and 20 show an intervertebral disk prosthesis 60 according to a fourth embodiment of the present invention. In this embodiment, the upper and lower plates 61, 62 are reversed with respect to the previous embodiments. Thus, lower plate 62 and core 63 have first coupling means enabling movements of flexion/extension and/or lateral tilting of lower plate 62 relative to upper plate 61 in two phases. These first coupling means consist of tilted studs 64 that project on the articular surface of lower plate 62 in a sagittal plane and corresponding cavities 65 that are formed in the lower articular surface of core 63. During the first phase of the above-mentioned movements, studs 64 move freely in cavities 65. During the second phase, core 63 is driven with lower plate 62 by studs 64. Second coupling means are also provided, between upper plate 61 and core 63. These second coupling means comprise a mobile intermediate guide part 66 provided partly in a first groove 67 that is formed in the articular surface of upper plate 61 and is oriented in a sagittal direction and partly in a second groove 68 that is formed in the upper articular surface of core 63 and is oriented in a frontal direction. The radius of curvature of the upper articular surface of core 63 and of the articular surface of upper plate 61 is less than the radius of curvature of the lower articular surface of core 63 and of the articular surface of lower plate 62, as in the previous embodiments.

The present invention has been described above only by way of example. It will appear clearly to one skilled in the art that modification can be made without exceeding the scope of the invention. For example, the projecting portions 11, 28, 48, 64 could be provided on core 4, 23, 43, 63 rather than on upper plate 2, 21, 41 or lower plate 62, and the corresponding cavities 12, 29, 49, 65 could be formed in upper plate 2, 21, 41 or lower plate 62 rather than in core 4, 23, 43, 63. Comparably, rail 13 or studs 50 could be provided on core 4, 43 rather than on lower plate 3, 42 and corresponding groove 15 or corresponding cavities 51 could be formed in lower plate 3, 42 rather than in core 4, 43.

The invention claimed is:

1. An intervertebral disk prosthesis comprising:
   first and second parts intended to be attached respectively to two adjacent vertebrae,
   an intermediate part inserted between the first and second parts and comprising articular surfaces that cooperate with respective articular surfaces of the first and second parts, and
   means for coupling the first part and the intermediate part, wherein the coupling means are arranged to leave the intermediate part free relative to the first part during a first phase of a tilting movement of the first part relative to the second part, such that the intermediate part is displaced toward an end of the prosthesis that is opposite to an end toward which the first part is displaced by tilting relative to the second part, and to drive the intermediate part with the first part during a second phase of the tilting movement, said tilting movement being in the same direction in the second phase as in the first phase,
   wherein the first and second parts when placed in the vertebrae are not in abutment during said second phase.

2. The intervertebral disk prosthesis according to claim 1, wherein said coupling means comprise at least one projecting portion provided on one of the first part and intermediate part and at least one cavity formed in the other of the first part and intermediate part, whereby this cavity receives the projecting portion and has a larger section than that of the projecting portion.

3. The intervertebral disk prosthesis according to claim 2, wherein said coupling means comprise a single projecting portion provided on a peripheral portion of the first part or the intermediate part and located in a sagittal plane.

4. The intervertebral disk prosthesis according to claim 2, wherein said coupling means comprise first and second projecting portions provided on the first part or the intermediate part and located in a sagittal plane, on both sides of the axis of the prosthesis, and first and second corresponding cavities formed in the intermediate part or the first part respectively.

5. The intervertebral disk prosthesis according to claim 1, further comprising means for coupling the intermediate part and the second part, whereby these coupling means limit the relative movements in axial rotation of said intermediate part and second part.

6. The intervertebral disk prosthesis according to claim 5, wherein said means for coupling the intermediate part and the second part comprise a rail extending in a sagittal direction on one of the second part and intermediate part and a groove formed in the other of the second part and intermediate part and cooperating with this rail.

7. The intervertebral disk prosthesis according to claim 6, wherein the rail and the groove define respective inclined support surfaces that cooperate during flexion movements of the prosthesis to slightly raise the center of gravity of the intermediate part.

8. The intervertebral disk prosthesis according to claim 5, wherein said means for coupling the intermediate part and the second part comprise a first groove formed in the second part and oriented in a sagittal direction, a second groove formed in the intermediate part and oriented in a frontal direction, and a mobile guide part cooperating with the first and second grooves.

9. The intervertebral disk prosthesis according to claim 8, wherein a play is provided between the guide part and at least one of the first and second grooves, allowing axial-rotation travel of the intermediate part relative to the second part.

10. The intervertebral disk prosthesis according to claim 5, wherein said means for coupling the intermediate part and the second part comprise first and second studs provided on the second part or the intermediate part and located in a frontal plane, on both sides of the axis of the prosthesis, and first and second cavities formed in the intermediate part or the second part, respectively, and receiving the studs.

11. The intervertebral disk prosthesis according to claim 1, wherein the first phase of the tilting movement corresponds to about 40 to 60% of the maximum tilting angle of the first part relative to the second part, and the second phase corresponds to the remaining 60 to 40%.

12. The intervertebral disk prosthesis according to claim 1, wherein the first phase of the tilting movement corresponds to an angular tilting range of the first part relative to the second part of about 4 to 8°, and the second phase of the tilting movement corresponds to an angular tilting range of the first part relative to the second part of about 3 to 7°.

13. The intervertebral disk prosthesis according to claim 1, wherein the first phase of the tilting movement corresponds to an angular tilting range of the first part relative to the second part of about 5 to 7°, and the second phase of the tilting movement corresponds to an angular tilting range of the first part relative to the second part of about 4 to 6°.

14. The intervertebral disk prosthesis according to claim 1, wherein said articular surfaces of the intermediate part are convex, and said respective articular surfaces of the first and second parts are concave.

15. The intervertebral disk prosthesis according to claim 1, wherein the articular surface of the first part and the corresponding articular surface of the intermediate part are spherical portions of radius R1, and the articular surface of the second part and the corresponding articular surface of the intermediate part are spherical portions of radius R2.

16. The intervertebral disk prosthesis according to claim 15, wherein the first part is an upper part, the second part is a lower part, and the radius R1 is less than the radius R2.

17. The intervertebral disk prosthesis according to claim 1, wherein the first part is a lower part, the second part is an upper part and the means for coupling the first part and the intermediate part comprise first and second projecting portions provided on the first part or the intermediate part and located in a sagittal plane on both sides of the axis of the prosthesis and first and second corresponding cavities formed in the intermediate part or in the first part respectively, the prosthesis further comprising second coupling means for coupling the second part and the intermediate part, these second coupling means comprising a first groove formed in the second part and oriented in a sagittal direction, a second groove formed in the intermediate part and oriented in a frontal direction, and a mobile guide part cooperating with the first and second grooves.

18. The intervertebral disk prosthesis according to claim 17, wherein the articular surface of the first part and the corresponding articular surface of the intermediate part are spherical portions of radius R1, and the articular surface of the second part and the corresponding articular surface of the intermediate part are spherical portions of radius R2, whereby the radius R2 is less than the radius R1.

* * * * *